(12) United States Patent
Howard

(10) Patent No.: US 8,357,422 B2
(45) Date of Patent: Jan. 22, 2013

(54) DIETARY SUPPLEMENT

(75) Inventor: Clinton Howard, Irving, TX (US)

(73) Assignee: RBC Life Sciences, Inc., Irving, TX (US)

( * ) Notice: Subject to any disclaimer, the term of this patent is extended or adjusted under 35 U.S.C. 154(b) by 374 days.

(21) Appl. No.: 12/830,051

(22) Filed: Jul. 2, 2010

(65) Prior Publication Data

US 2012/0003378 A1    Jan. 5, 2012

(51) Int. Cl.
*A01N 65/00*        (2009.01)
*A61K 36/9606*    (2006.01)
*A61K 36/16*       (2006.01)
*A23J 7/00*         (2006.01)
*C07D 311/30*     (2006.01)

(52) U.S. Cl. .................... 426/648; 424/725; 424/752
(58) Field of Classification Search .................. None
See application file for complete search history.

(56) References Cited

U.S. PATENT DOCUMENTS

| | | | |
|---|---|---|---|
| 6,964,969 B2 | 11/2005 | McCleary | |
| 7,579,026 B2 | 8/2009 | Myhill | |
| 7,923,041 B2 | 4/2011 | Stock | |
| 7,923,045 B2 | 4/2011 | Myhill | |
| 7,972,633 B2 | 7/2011 | Smith | |
| 2001/0043952 A1 * | 11/2001 | Saito | |
| 2002/0182196 A1 | 12/2002 | McCleary | |
| 2004/0001817 A1 | 1/2004 | Giampapa | |
| 2005/0158396 A1 | 7/2005 | Kraechter | |
| 2006/0014773 A1 | 1/2006 | McCleary | |
| 2006/0078533 A1 | 4/2006 | Omoigui | |
| 2006/0275294 A1 | 12/2006 | Omoigui | |
| 2007/0253941 A1 | 11/2007 | Naidu | |
| 2008/0213401 A1 | 9/2008 | Smith | |
| 2008/0213406 A1 | 9/2008 | Stock | |
| 2009/0311350 A1 | 12/2009 | Myhill | |

FOREIGN PATENT DOCUMENTS

| WO | 2006/066987 A1 | 6/2006 |
|---|---|---|
| WO | 2008/152444 A2 | 12/2008 |

* cited by examiner

*Primary Examiner* — Michele C. Flood
(74) *Attorney, Agent, or Firm* — Shaukat A. Karjeker; Mark D. Perdue

(57) ABSTRACT

The technology provides a multi-purpose dietary supplement that includes, in nutritionally effective amounts for humans, an orally ingestible combination of antioxidants, naturally-occurring substances and extracts of naturally-occurring substances. The naturally-occurring substances and extracts of naturally-occurring substances include at least: finely divided silica hydride; a polyphenol; *ginkgo biloba* leaf extract; *rhodiola rosea* root; *bacopa monniera* extract; a glutathione precursor; a phytoalexin; a bioflavonoids; CoQ10 and a phospholipid.

22 Claims, No Drawings

DIETARY SUPPLEMENT

BACKGROUND

1. Technical Field

The technology relates to dietary supplements for human ingestion, and more particularly to supplements that include powerful antioxidants and a plurality of naturally-occurring components and/or components derived from naturally-occurring substances.

2. Description of the Related Art

In recent years there has been continuing and growing interest in foods and the potential health benefits of a diet that incorporates certain kinds of foods, and minimizes other kinds of foods. The so-called "food pyramid" has been revised in an attempt to influence the diet of the population toward foods that are currently believed will better maintain health. At the same time, there has been growing concern among sectors of the population regarding the nature of the available food supply. For example, is it "natural" as opposed to genetically engineered? Is it organically grown using only "natural fertilizers" and free of chemical fertilizers and pesticides? Is it sustainably farmed? Is it free of added hormones? As a result, consumers have many choices about the foodstuffs they can consume, and have some guidance, based on current understanding of human dietary requirements, of what constitutes a healthy diet.

Despite the increased consumer awareness of diet and its potential effects on health, the typical diet often lacks essential amounts of certain necessary elements. For example, many still have lower than recommended intake of calcium to strengthen bones and maintain bone density. Others may lack certain vitamins, or minerals like zinc or magnesium. In addition, there is a growing awareness that certain foods and herbs may include important elements for maintaining health, even though these may not be found in significant amounts in the "food pyramid diet." Accordingly, there has lately been a strong interest in particular fruits, berries and vegetables, such as acai berries, broccoli, and pomegranates. In addition, there has been growing interest in ancient herbs and teas, such as rooibos tea that has high levels of anti-oxidants which may reduce the levels and harmful effects of free radicals in the body. There has also been significant interest in newly-developed food extracts, such as omega-3 fatty acids derived from certain fish and flax seeds, to promote cardio-vascular health.

SUMMARY

An exemplary embodiment provides a multi-purpose dietary supplement that includes, in nutritionally effective amounts for humans, an orally ingestible combination of antioxidants, naturally-occurring substances, and extracts of naturally-occurring substances. The antioxidants, naturally-occurring substances, and extracts of naturally-occurring substances may include:
- Microhydrin®;
- a polyphenol;
- *ginkgo biloba* leaf extract;
- *rhodiola rosea* root;
- *bacopa monniera* extract;
- a glutathione precursor;
- a phytoalexin;
- a bioflavonoid; and
- a phospholipid.

Microhydrin® is a federally registered trademark of RBC Life Sciences, Inc. of Irving, Tex. It is a powerful antioxidant that includes, as a principal ingredient, $SiH_2$.

In particular examples of the exemplary embodiment, the polyphenol may include curcumin extracted from turmeric. Further, the glutathione precursor may include N-acetyl-cysteine. The phytoalexin may include resveratrol. The bioflavonoids may include any one or more of: quercetin and the citrus bioflavonoids. In addition, the supplement may include CoQ10. In an exemplary embodiment, the phospholipid may be any one of phosphatidyl choline and phosphatidyl serine.

In another exemplary embodiment, there is provided a multi-purpose dietary supplement comprising, in nutritionally effective amounts for humans, an orally ingestible combination of antioxidants, naturally-occurring substances and extracts of naturally-occurring substances. The antioxidants, naturally-occurring substances, and extracts of naturally-occurring substances may include:
- from about 30 to about 1000 mg Microhydrin®
- from about 50 mg to about 400 mg of a polyphenol;
- from about 40 mg to about 320 mg *ginkgo biloba* leaf extract;
- from about 50 mg to about 400 mg. *rhodiola rosea* root;
- from about 50 mg to about 400 mg *bacopa monniera* extract;
- from about 25 mg to about 200 mg of a glutathione precursor;
- from about 20 mg to about 160 mg of a phytoalexin;
- from about 75 mg to about 600 mg bioflavonoids; and
- from about 80 mg to about 660 mg of a phospholipid.

In another exemplary embodiment, the antioxidants, naturally-occurring substances and extracts of naturally-occurring substances may include the following composition:
- about 12.7 wt. % of a polyphenol;
- about 10.2 wt. % *ginkgo biloba* leaf extract;
- about 12.7 wt. % *rhodiola rosea* root;
- about 12.7 wt. % *bacopa monniera* extract;
- about 6.4 wt. % of a glutathione precursor;
- about 5.1 wt. % of a phytoalexin;
- about 19.1 wt. % bioflavonoids; and
- about 21.1 wt. % of a phospholipid.

In addition to the foregoing proportions of the naturally-occurring substances and extracts of the latter exemplary embodiment, the nutritional supplement includes Microhydrin® in a mass proportion of from about 8 parts Microhydrin® per 100 parts naturally occurring substances and extracts, to about 100 parts Microhydrin® to about 100 parts naturally occurring substances and extracts.

A further exemplary embodiment of a dietary supplement includes, in nutritionally effective amounts, an orally ingestible combination of antioxidants, naturally-occurring substances and extracts of naturally-occurring substances. The antioxidants, naturally-occurring substances and extracts of naturally-occurring substances may include:
- finely divided silica hydride;
- turmeric extract;
- *ginkgo biloba* leaf extract;
- *rhodiola rosea* root;
- *bacopa monniera* extract;
- N-acetyl-cysteine;
- resveratrol;
- quercetin;
- citrus bioflavonoids; and
- at least one of phosphatidyl choline and phosphatidyl serine.

In an exemplary embodiment, the orally ingestible multi-purpose dietary supplement is formulated appropriately from natural botanicals and powerful antioxidants to enhance cellular health and life. The exemplary supplement may be administered in a single daily dose or multiple doses per day, in sufficient quantity so that the supplement has the desired multiple neurological effects. The dose may be in the form of one or more capsules, tablets or as a measured amount of a powder. The desired effects include supporting and defending healthy brain function, and enhancing the ability to think, remember and learn.

DETAILED DESCRIPTION

It appears that free radicals may be a major culprit in the aging process, and in damaging cells of the body, including cells of the brain, leading to cognitive impairment that worsens with age. Free radicals may be neutralized in the body by combining with antioxidants. Antioxidants are found widely in foods, such as fruits, vegetables, dark chocolate, red wine and green tea. Eating a diet high in antioxidants may act to protect brain cells.

The technology provides exemplary multi-purpose dietary supplements for human consumption through oral ingestion. While these multi-purpose dietary supplements are formulated to protect and improve neurological functions, they may also have other effects that contribute to a better, healthier life. The desired effects of the dietary supplements include supporting and defending healthy brain function, and enhancing the ability to think, remember and learn.

The dietary supplements are formulated to include natural botanical products and their extracts and powerful antioxidants. In an exemplary embodiment, a synergist or "activity-enhancer," Microhydrin®, which is also a powerful antioxidant, is added. Microhydrin® is a federally registered trademark of RBC Life Sciences, Inc. of Irving, Tex. It is theorized, without being bound, that the synergist enhances or improves the bioavailability of the other active ingredients, and facilitates synergistic interactions between them to enhance their activity and performance in the body.

An exemplary embodiment of the multi-purpose dietary supplement is blended appropriately from natural botanicals and powerful antioxidants to enhance cellular health and life. The exemplary supplement may be administered in a single daily dose or multiple doses per day, in sufficient quantity so that the supplement has the desired neurological effects. These desired effects include supporting and defending healthy brain function, and enhancing the ability to think, remember and learn. Appropriate dosage may be supplied in a powdered encapsulated form, taken once, twice or more times daily, as recommended.

Other exemplary embodiments of the multi-purpose dietary supplement may provide at least some, and in many cases all, of the following exemplary benefits: enhancing total plasma antioxidant capacity, reducing dismutase activity in erythrocytes, improving endurance exercise, protecting body cells against oxidative stress, restoring and maintaining normal serotonin levels in the hippocampus, reducing exercise-induced fatigue, improving memory retention of new information, improving working memory (e.g. spatial accuracy), reducing beta amyloid deposits in the brain (associated with Alzheimer's Disease), suppressing Lldr gene expression and reducing cellular LDL cholesterol, reducing the risks of development of type II diabetes, reducing chronic inflammatory responses, reducing risks of developing hypertension, and enhancing muscle performance to reduce muscle tissue damage from exercise. The foregoing benefits include cardiovascular, neurological and cognitive, anti-depressive, anti-inflammatory and health maintenance benefits. Accordingly, the exemplary embodiment of the multi-purpose supplement may be formulated with appropriate proportions of active ingredients to provide a range of benefits when taken in a single recommended daily dose, or in multiple daily recommended doses.

In general, active ingredients or "active components" of the exemplary multi-purpose supplements should be present in sufficient quantity in each daily supply, which may include one or more daily doses, to be effective. Thus, for example, for a two-component supplement, if the daily effective dose of component A is $x_A$ grams, and of component B is $x_B$, then the daily dose should contain $x_A$ grams of component A and $x_B$ grams of component B. Generalizing, therefore, for a supplement having n active components, each of the n components should be present in its respective effective amount. Thus, the supplement dose is the sum of the $x_1, x_2 \ldots x_n$ grams. This should ensure that each of the n active components is present in an amount sufficient to provide its full beneficial effect to the patient. However, according to exemplary embodiments of the multi-purpose dietary supplements, some of the active ingredients may overlap in their beneficial effects and some may complement each other, thereby reducing the total dosage necessary. In addition, exemplary embodiments may include an activity-enhancing component that enhances the activity of the active ingredient(s). It is theorized, without being bound, that the activity-enhancing component may promote the absorption of the active ingredient(s) into the blood stream and may also enhance activity once so absorbed. Regardless of the theory, the activity-enhancing component (Microhydrin®) increases the activity of exemplary embodiments of the multi-purpose dietary supplements that contain this component.

An exemplary embodiment of the multi-purpose dietary supplements includes Microhydrin® and at least some of the following naturally-occurring substances and extracts of naturally-occurring substances as active ingredients:

a polyphenol;
   *ginkgo biloba* leaf extract;
   *rhodiola rosea* root;
   *bacopa monniera* extract;
   a glutathione precursor;
   a phytoalexin;
   Coenzyme Q10 ("CoQ10");
   citrus bioflavonoids;
   a bioflavonoid; and
   a phospholipid.

The Microhydrin® is an activity-enhancing component because, when the supplement is ingested, its presence increases the bioavailability of other active ingredients in the multi-purpose dietary supplement. Microhydrin® is therefore a recommended activity-enhancer. It is a product obtainable from RBC Life Sciences, Inc. of Irving, Tex., and from outlets in the USA and elsewhere. Microhydrin® is a proprietary substance formulated in a process that blends several chemical compounds. Microhydrin® includes, among other ingredients, finely divided silica hydride potassium carbonate, magnesium ascorbate, potassium citrate, silica, purified-ionized water, calcium hydroxide, mannitol, ascorbic acid, magnesium sulfate, citric acid, and sunflower seed oil. Tests confirm that Microhydrin® includes silica nano-particles of average height 5.9 nm and that some clustering is present. It is a powerful antioxidant. U.S. Patent Publication number 2003/0190374, published Oct. 9, 2003, is hereby incorporated by reference for its disclosures about silica hydride. Microhydrin® is not a naturally-occurring substance nor is it an extract of naturally-occurring substances. It is essentially a mineral additive, and is not synthetic because all its components occur naturally.

The polyphenol of the above exemplary embodiment of a dietary supplement may be selected from one or more of the naturally-occurring plant polyphenols. These include, for example, turmeric extract (which contains curcumin, essential oils, among other chemicals) curcuma longa, ginger and the like. Curcumin is a powerful antioxidant and it exhibits antioxidant and anti-neurodegenerative properties. It has also been found to suppress the low density lipoprotein (LDL) receptor thereby inhibiting LDL-induced activation of hepatic stellate cells. It suppressed Lldr gene expression and reduced cellular cholesterol. It may be useful in reducing the risk of hypercholesterolemia-associated hepatic fibrogenesis.

*Ginkgo biloba* leaf extract contains flavonoids, glycosides and terpenoids. *Ginkgo biloba* has anticholinesterase and antiamnestic properties. It has beneficial neurological effects.

*Rhodiola rosea* root contains higher molecular weight proanthocyanidins and is derived from a plant of the Crassulaceae family. The Crassulaceae family also includes *R. alterna, R. brevipetiolata, R. crenulata, R. kirilowii, R. quadrifida, R. sachalinensis*, and *R. sacra*. The powdered root of these may be substituted for *R. rosea* root, taking into account any variations in activity and adjusting quantity in the dose appropriately. This active ingredient enhances plasma antioxidant capacity and reduces superoxide dismutase in erythrocytes. *Rhodiola rosea* restores normal brain serotonin levels (i.e., it enhances mood and mental performance) and restores neural cell proliferation. High levels can improve endurance exercise capacity in young patients. Further, it has reduced exercise-induced fatigue.

*Bacopa monniera* extract is derived from a perennial creeping herb. The extract may improve mental focus (mental concentration) and working memory performance; i.e. spatial accuracy. It enhances cognitive activity and retention of new information ("memory"). It has also reduced the formation of beta amyloid brain plaque, and deposits of this plaque, which are associated with Alzheimer's Disease. In smokers, it has maintained trace elements of zinc, copper, iron and selenium that are typically reduced by smoking. It also improved activities of antioxidant superoxide dismutase, catalse, glutathione peroxidase, and glutathione reductase that are each suppressed in smokers.

The glutathione precursor may be selected from N-acetyl cysteine, Alpha-lipoic acid, Glycine, Cycteine, Silymarin, Melatonin, L-glutamine and the like. N-acetyl cysteine augments cytokine production and is one of the body's natural protective compounds. It is also said to reduce oxidative stress in the brain.

The phytoalexin of the above exemplary dietary supplement may be selected from Resveratrol (trans-Resveratrol), obtained from the skin of red grapes. Resveratrol prevents hyperglycemia-induced endothelial dysfunction by activation of adenosine monophosphate-activated protein kinase. Resveratrol may therefore act as a prophylactic to delay or prevent the onset of type II diabetes. Further, it may reduce plaque associated with age-related cognitive impairment. Resveratrol also has anti-inflammatory, antioxidant and anti-proliferative effects on pulmonary arteries and may prevent or delay the onset of hypertension and associated cardio-vascular disease.

CoQ10 (which is Coenzyme Q10, also known as Ubiquinone) is chemically known as 1, 4-benzoquinone. It is present in most eukaryotic cells, and in the mitochondria, in particular. It is a powerful antioxidant and is used in body cells to produce energy. Brain levels of CoQ10 decline with age, and this decline is associated with cognitive impairment. Accordingly supplementation with CoQ10 may be expected to arrest and possibly reverse age-related cognitive impairment. It also has properties that may enhance athletic performance and reduce fatigue. It protects neurons from stress and therefore has neurological benefits. Further, it preserves glutathione levels and prevents elevation of the stress marker, malondialdehyde (MDA).

Phospholipids include, among others, phosphatidyl choline and phosphatidyl serine. The phospholipids enhance exercise capacity, reduce fatigue onset, and reduce exercise-induced muscle damage. Further, the phospholipids, especially phosphatidyl serine, a fat naturally found in the brain, enhance cognitive function and reduce cognitive dysfunction.

Bioflavonoid may be selected from plant-derived quercetin, catachins (flavanol) derived from camellia sinensis or theobroma cacao, and the like. Quercetin is a powerful antioxidant and it has beneficial effects in protecting brain cells from oxidative damage that might cause a decline in mental acuity. It also has beneficial effects on the liver through enhancing the antioxidant enzyme activity and reducing pro-oxidant effects and thereby reducing or preventing fibrosis of the liver. It also reverses age-related decrease in glutathione and catalase levels.

Citrus flavonoids include those obtained from lemons, grapefruit, oranges and limes, for example. These, in conjunction with other active ingredients, reduce oxidative stress.

In an exemplary embodiment, each active component is present in an effective amount sufficient to obtain nutritional benefit. Thus, for example, the effective amounts in a multi-purpose dietary supplement may be as follows:

TABLE I

| Component | Mass (mg) | Range of mass per dose |
|---|---|---|
| Activity-enhancer (e.g. Microhydrin ®) | 100.0 | 50 mg to 800 mg |
| Phosphatidyl choline | 62.5 | 30 mg to 500 mg |
| Turmeric Extract | 50.0 | 25 mg to 400 mg |
| *Rhodiola rosea* | 50.0 | 25 mg to 400 mg |
| Citrus bioflavonoids | 50.0 | 25 mg to 400 mg |
| *Bacopa monniera* extract | 50.0 | 25 mg to 400 mg |
| *Ginkgo Biloba* (leaf powder) | 40.0 | 20 mg to 320 mg |
| Quercetin | 25.0 | 12.5 mg to 200 mg |
| N-acetyl cysteine | 25.0 | 12.5 mg to 200 mg |
| Phosphatidyl serine | 20.0 | 10 mg to 160 mg |
| Resveratrol (root) | 20.0 | 10 mg to 160 mg |
| CoQ10 | 10.0 | 5 mg to 80 mg |

The range of mass per dose specified in the above table may differ in other embodiments, and the numerical values should each be read as indicating "from about x (lower limit) to about y (upper limit)" rather than as exact limits. Thus, for example, phosphatidyl choline content is from about 30 mg to about 500 mg.

The mass quantities and weight percentages of the foregoing table may be amended when substitutions are made for specific active ingredients, and the substitutes are either more or less active. Thus, if a less active ingredient is substituted for N-acetyl cysteine, for example, then a greater quantity may be needed, and a correspondingly higher wt. % of that substitute ingredient.

In general, based on the exemplary formulation in the above table, a daily dose is about 512.5 mg, not including any fillers, adjuvants and the like. This may be administered orally once a day, or may be divided into two or three doses taken at intervals throughout the day, as may be convenient and appropriate for the patient.

In another exemplary embodiment, some of the following naturally-occurring substances and extracts of naturally-occurring substances as active ingredients are specific, while others may include any active member of a family, such as the polyphenols. The proportions of each of the components may be tabulated as follows:

TABLE II

| Component | Mass (mg) |
| --- | --- |
| Microhydrin | about 80 mg |
| Polyphenol | about 50 mg |
| Ginkgo Biloba leaf extract | about 40 mg |
| Rhodiola root | about 50 mg |
| Bacopa monniera extract | about 50 mg |
| Glutathione precursor | about 25 mg |
| Phospholipid | about 80 mg |
| Phytoalexin | about 20 mg |
| Bioflavonoid | about 75 mg |

The mass quantities (and implicit weight percentages) of the foregoing table may be amended when substitutions are made for specific active ingredients, and the substitutes are either more or less active. Thus, if a less active *Rhodiola* species is substituted for *Rhodiola rosea*, for example, then a greater quantity may be needed, and a correspondingly higher wt. % of that substitute ingredient.

While several exemplary embodiments have been presented in the foregoing detailed description of the invention and in the following non-limiting example, it should be appreciated that a multiplicity of variations exists. It should also be appreciated that the exemplary embodiment or exemplary embodiments are only examples, and are not intended to limit the scope or applicability of the technology in any way. Rather, the foregoing detailed description will provide those skilled in the art with a convenient road map for implementing an exemplary embodiment of the invention, it being understood that various changes may be made in the specific components described in an exemplary embodiment without departing from the scope of the invention, as set forth in the appended claims and their legal equivalents.

EXAMPLE

Tests were conducted on rats to ascertain whether rats fed a diet that included an exemplary dietary supplement that included Microhydrin® had improved maze-learning cognitive capacity versus three other groups of rats. These three groups included a control group of rats without a dietary supplement, a group of rats fed the dietary supplement without Microhydrin®, and a group of rats fed Microhydrin® without the dietary supplement. Further, tests were conducted to determine whether the ability to learn could be maintained as rats age.

The test utilized 72 male Fisher-Norway hybrid rats that were vigorous explorers of mean lifespan 34.5 months. Equal numbers of young (2-3 month old) and old (22 month old) rats were assigned to each of 4 groups, based on diet. Group 1 was a control group fed Rat Chow. Group 2A was fed Rat Chow plus a high dose of an exemplary dietary supplement including Microhydrin®. Group 2B was fed Rat Chow plus a low dose of the exemplary dietary supplement including Microhydrin®. Group 3A was fed Rat Chow plus a high dose of Microhydrin®. Group 3B was fed Rat Chow plus a low dose of Microhydrin®. Group 4A was fed Rat Chow with only a high dose of dietary supplement, without Microhydrin®. Group 4B was fed Rat Chow with only a low dose of dietary supplement, without Microhydrin®.

In each of the Groups, the dietary supplement was formulated in proportion as follows, in milligrams:

TABLE III

| | |
| --- | --- |
| Microhydrin ® (only Groups 2A, 2B, 3A, and 3B) | 100.0 |
| Phosphatidyl choline | 62.5 |
| Turmeric extract | 50.0 |
| Rhodiola rosea | 50.0 |
| Citrus bioflavonoids | 50.0 |
| Bacopa monniera extract | 50.0 |
| Ginkgo biloba (leaf powder) | 40.0 |
| Quercetin | 25.0 |
| N-acetyl cysteine | 25.0 |
| Phosphatidyl serine | 20.0 |
| Resveratrol (root) | 20.0 |
| CoQ10 | 10.0 |

Rats were fed their respective Group diets for four weeks. Rats were acclimated to a maze for 1 week before testing, and for 40 days thereafter.

Young Rats

The results comparing young rats of the control versus the "low dose" young rats of Groups 2B, 3B and 4B showed a marked decrease in the number of days to learn a maze in the rats of Group 2B fed antioxidants that included Microhydrin®. The rats of Group 2B took about 7 days, whereas the rats of the control took 13 days. Further, rats of Group 3B took 18 days, while those of Group 4B took 14-15 days to learn the maze. Thus, the addition of the supplement containing Microhydrin® made a significant beneficial difference in maze-learning speed.

Further, as to the "high dose" young rats of Groups 2A, 3A and 4A, these also showed the lowest number of days (6) to learning a maze for the rats of Group 2A (dietary supplement plus Microhydrin®). Next were rats of Group 3A at 9 days, and Group 4A at 11 days. The control rats took 13 days.

Aging Rats

The results comparing aging rats of the control versus the "low dose" aging rats of Groups 2B, 3B and 4B also showed a decrease in the number of days to learn a maze when Microhydrin® was added to the dietary supplement, as in Group 2B. The rats of Group 2B took about 24 days, whereas the rats of the control took 27 days. Further, rats of Group 3B took 20 days, while those of Group 4B took 24-25 days to learn the maze. Thus, the addition at low doses of the supplement containing Microhydrin®, and Microhydrin® by itself, made a significant (but not marked) beneficial difference in maze-learning speed.

Further, as to the "high dose" aging rats of Groups 2A, 3A and 4A, these also showed the lowest number of days (17) to learning a maze for the rats of Group 2A (dietary supplement plus Microhydrin®). Next were rats of Group 4A at 17 days, and Group 3A at 22 days. The control rats took 27 days. Thus, the addition at high doses of the dietary supplement containing Microhydrin® was more effective than the supplement by itself without Microhydrin®, and was also more effective than Microhydrin® by itself or the control in maze-learning speed.

Tests were also conducted on the Groups of rats to ascertain whether Microhydrin® added to a dietary supplement restores and/or protects the learning capacity of rats as they age over time, relative to rats fed the dietary supplement by itself, without Microhydrin®, and relative to rats fed Microhydrin® by itself.

The results indicate that the "low dose" rats of Group 2B had virtually no learning impaired rats. The control showed 40% learning impaired. The rats of Group 4B (low dose dietary supplement without Microhydrin®) had about 45% learning impaired, while those on Microhydrin® alone (Group 3B) showed about 22% learning impaired. Thus, even at low doses, rats fed a dietary supplement with Microhydrin® exhibit markedly better rates of learning capacity maintenance. Or, put another way, groups of rats fed a dietary supplement with Microhydrin® exhibit fewer, if any, members with learning capacity impairment.

The results indicate that the "high dose" rats of Group 2A had virtually no learning impaired rats. The control showed 40% learning impaired. The rats of Group 4A (high dose dietary supplement without Microhydrin®) had about 18% learning impaired, while those on Microhydrin® alone (Group 3B) showed about 24% learning impaired. Thus, at high doses, rats fed a dietary supplement with Microhydrin® exhibit markedly better rates of learning capacity maintenance. Or, put another way, groups of rats fed a dietary supplement with Microhydrin® exhibit fewer, if any, members with learning capacity impairment.

The invention claimed is

1. A multi-purpose dietary supplement comprising, in nutritionally effective amounts for humans, an orally ingestible combination of antioxidants, naturally-occurring substances and extracts of naturally-occurring substances, the antioxidants and naturally-occurring substances and extracts of naturally-occurring substances comprising:
   Microhydrin®;
   a polyphenol;
   *ginkgo biloba* leaf extract;
   *rhodiola rosea* root;
   *bacopa monniera* extract;
   a glutathione precursor;
   a phytoalexin;
   a bioflavonoid; and
   a phospholipid.

2. The supplement of claim 1, wherein the polyphenol comprises curcumin extracted from turmeric.

3. The supplement of claim 1, wherein the glutathione precursor comprises N-acetyl-cysteine.

4. The supplement of claim 1, wherein the phytoalexin comprises resveratrol.

5. The supplement of claim 1, wherein the bioflavonoids comprise any one or more of quercetin and a citrus bioflavonoid.

6. The supplement of claim 1, further comprising Coenzyme Q10 (CoQ10).

7. The supplement of claim 1, wherein the phospholipid comprises any one of phosphatidyl choline and phosphatidyl serine.

8. A multi-purpose dietary supplement comprising, in nutritionally effective amounts for humans, an orally ingestible combination of antioxidants, naturally-occurring substances and extracts of naturally-occurring substances, the antioxidants and naturally-occurring substances and extracts of naturally-occurring substances comprising:
   about 30 to about 1000 mg Microhydrin®;
   about 50 mg to about 400 mg of a polyphenol;
   about 40 mg to about 320 mg *ginkgo biloba* leaf extract;
   about 50 mg to about 400 mg *rhodiola rosea* root;
   about 50 mg to about 400 mg *bacopa monniera* extract;
   about 25 mg to about 200 mg of a glutathione precursor;
   about 20 mg to about 160 mg of a phytoalexin;
   about 75 mg to about 600 mg bioflavonoids; and
   about 80 mg to about 660 mg of a phospholipid.

9. The supplement of claim 8, wherein the polyphenol comprises curcumin extracted from turmeric.

10. The supplement of claim 8, wherein the glutathione precursor comprises N-acetyl-cysteine.

11. The supplement of claim 8, wherein the phytoalexin comprises resveratrol.

12. The supplement of claim 8, wherein the bioflavonoids comprise any one or more of quercetin and a citrus bioflavonoid.

13. The supplement of claim 8, further comprising silica hydride.

14. The supplement of claim 8, further comprising about 5 to about 80 mg CoQ10.

15. The supplement of claim 8, wherein the phospholipid comprises any one of phosphatidyl choline and phosphatidyl serine.

16. A dietary supplement comprising, in nutritionally effective amounts, an orally ingestible combination of antioxidants, naturally-occurring substances and extracts of naturally-occurring substances, the antioxidants, naturally-occurring substances and extracts of naturally-occurring substances comprising:
   Microhydrin®;
   turmeric extract;
   *ginkgo biloba* leaf extract;
   *rhodiola rosea* root;
   *bacopa monniera* extract;
   N-acetyl-cysteine;
   resveratrol;
   quercetin;
   citrus bioflavonoids; and
   at least one of phosphatidyl choline and phosphatidyl serine.

17. The supplement of claim 16, further comprising about 5 to about 80 mg CoQ10.

18. The supplement of claim 16, comprising about 25 to about 400 mg turmeric extract.

19. The supplement of claim 16, comprising about 25 to about 400 mg *rhodiola rosea* root.

20. The supplement of claim 16, comprising about 25 to about 400 *bacopa monniera* extract.

21. The supplement of claim 16, comprising about 12.5 to about 200 mg quercetin.

22. The supplement of claim 16, comprising about 50 to about 800 mg Microhydrin®.

* * * * *